US011344502B1

(12) United States Patent
Dihora et al.

(10) Patent No.: US 11,344,502 B1
(45) Date of Patent: May 31, 2022

(54) VITAMIN DELIVERY PARTICLE

(71) Applicant: TRUCAPSOL LLC, Bethlehem, PA (US)

(72) Inventors: Jiten Odhavji Dihora, Center Valley, PA (US); Caroline Rachel Multari, Bethlehem, PA (US)

(73) Assignee: TRUCAPSOL LLC, Bethlehem, PA (US)

( * ) Notice: Subject to any disclaimer, the term of this patent is extended or adjusted under 35 U.S.C. 154(b) by 0 days.

(21) Appl. No.: 16/287,509

(22) Filed: Feb. 27, 2019

Related U.S. Application Data

(60) Provisional application No. 62/650,038, filed on Mar. 29, 2018.

(51) Int. Cl.

| | |
|---|---|
| ***A61K 9/50*** | (2006.01) |
| ***A61K 47/42*** | (2017.01) |
| ***A61K 47/36*** | (2006.01) |
| ***A61K 47/26*** | (2006.01) |
| ***A61K 47/44*** | (2017.01) |
| ***A61K 47/02*** | (2006.01) |
| ***A61K 31/59*** | (2006.01) |
| ***A61K 31/07*** | (2006.01) |
| ***A61K 31/355*** | (2006.01) |
| ***A61K 31/375*** | (2006.01) |

(52) U.S. Cl.
CPC ............ *A61K 9/5036* (2013.01); *A61K 47/02* (2013.01); *A61K 47/26* (2013.01); *A61K 47/36* (2013.01); *A61K 47/42* (2013.01); *A61K 47/44* (2013.01); *A61K 31/07* (2013.01); *A61K 31/355* (2013.01); *A61K 31/375* (2013.01); *A61K 31/59* (2013.01)

(58) Field of Classification Search
None
See application file for complete search history.

(56) References Cited

U.S. PATENT DOCUMENTS

| | | | |
|---|---|---|---|
| 3,345,358 A | 10/1967 | Inklaar | |
| 3,819,838 A | 6/1974 | Smith et al. | |
| 5,550,189 A | 8/1996 | Qin et al. | |
| 5,574,179 A | 11/1996 | Wahl et al. | |
| 5,601,760 A | 2/1997 | Rosenberg | |
| 6,248,909 B1 | 6/2001 | Akimoto et al. | |
| 6,572,919 B2 | 6/2003 | Westland et al. | |
| 7,431,986 B2 | 10/2008 | Van Lengerich et al. | |
| 8,900,492 B2 | 12/2014 | Pacorel et al. | |
| 9,205,395 B2 * | 12/2015 | Yan | A61K 9/5057 |
| 9,332,774 B2 * | 5/2016 | Nakhasi | A21D 2/165 |
| 9,937,477 B2 | 4/2018 | Zhang et al. | |
| 9,993,401 B2 | 6/2018 | Barnett et al. | |
| 10,188,593 B2 | 1/2019 | Dihora et al. | |
| 2004/0017017 A1 * | 1/2004 | Van Lengerich | A23P 10/30 264/4 |
| 2004/0033264 A1 | 2/2004 | Sawhney | |
| 2005/0272628 A1 | 12/2005 | Meli et al. | |
| 2005/0276831 A1 | 12/2005 | Dihora et al. | |
| 2008/0167188 A1 | 7/2008 | Fischer et al. | |
| 2009/0209661 A1 | 8/2009 | Somerville Roberts et al. | |
| 2011/0052680 A1 * | 3/2011 | Hendrickson | A23P 10/30 424/451 |
| 2011/0268778 A1 | 11/2011 | Dihora et al. | |
| 2011/0268802 A1 | 11/2011 | Dihora et al. | |
| 2012/0128752 A1 | 5/2012 | Loo et al. | |
| 2013/0004617 A1 | 1/2013 | Zhang et al. | |
| 2013/0022654 A1 | 1/2013 | Deshmukh et al. | |
| 2013/0239429 A1 | 9/2013 | Vella et al. | |
| 2014/0199244 A1 | 7/2014 | Rijcken et al. | |
| 2014/0335032 A1 | 11/2014 | Panandiker et al. | |
| 2015/0252312 A1 | 9/2015 | de Villeneuve et al. | |
| 2016/0038428 A1 | 2/2016 | Harel et al. | |
| 2016/0128944 A1 | 5/2016 | Chawrai et al. | |
| 2016/0158121 A1 | 6/2016 | Lei et al. | |
| 2016/0166480 A1 | 6/2016 | Lei et al. | |
| 2016/0206561 A1 | 7/2016 | Kohane et al. | |
| 2016/0228338 A9 | 8/2016 | Dihora et al. | |
| 2017/0165627 A1 | 6/2017 | Duan et al. | |
| 2018/0015009 A1 | 1/2018 | Soubiran et al. | |

(Continued)

FOREIGN PATENT DOCUMENTS

| | | |
|---|---|---|
| EP | 0815743 A2 | 1/1998 |
| EP | 1371410 A1 | 12/2003 |
| EP | 1797946 A2 | 6/2007 |

(Continued)

OTHER PUBLICATIONS

Luo et al. (J Appl. Polym. Sci 2014 (2014).*
U.S. Appl. No. 15/642,708, filed Jul. 6, 2017 (now abandoned).
U.S. Appl. No. 16/282,993, filed Feb. 22, 2019.
U.S. Appl. No. 16/682,862, filed Nov. 13, 2019.
U.S. Appl. No. 16/830,152, filed Mar. 25, 2020.
U.S. Appl. No. 16/830,681, filed Mar. 26, 2020.
U.S. Appl. No. 16/853,003, filed Apr. 20, 2020.
International Search Report for PCT/US2017/037855, dated Nov. 2, 2017.
International Search Report for PCT/US2019/018959, dated Jul. 8, 2019.

(Continued)

*Primary Examiner* — Patricia Duffy
*Assistant Examiner* — Garen Gotfredson
(74) *Attorney, Agent, or Firm* — Caesar Rivise, PC

(57) ABSTRACT

Disclosed are controlled release particles including: (a) a core including at least one vitamin which is oil-soluble or oil-dispersible; and (b) a wall at least partially surrounding the core, wherein the controlled release particles are produced by reacting (i) a first composition including a hydrophobic oil, the at least one vitamin, an anti-oxidant and a wax with (ii) a second composition including a water soluble emulsifier, a corn protein and a solvent to form an intermediate product, which is mixed with (iii) a third composition including a cellulosic polymer in water, and dehydrated to provide the controlled release particles. A method for preparing the particles and compositions containing the particles are also disclosed.

18 Claims, 6 Drawing Sheets

(56) References Cited

U.S. PATENT DOCUMENTS

| | | | |
|---|---|---|---|
| 2018/0042825 A1* | 2/2018 | Lei | B32B 5/16 |
| 2019/0275490 A1 | 9/2019 | Bachawala | |

FOREIGN PATENT DOCUMENTS

| | | | |
|---|---|---|---|
| WO | 9901214 A1 | 1/1999 | |
| WO | 0105926 A1 | 1/2001 | |
| WO | 03013538 A1 | 2/2003 | |
| WO | 2006024411 A2 | 3/2006 | |
| WO | 2007135583 A2 | 11/2007 | |
| WO | 2016071151 A1 | 5/2016 | |
| WO | 2017023830 A1 | 2/2017 | |

OTHER PUBLICATIONS

Leung et al., "Enteric coating of micron-size drug particles through a Wurster fluid-bed process", Powder Technology, vol. 317, pp. 247-252 (2017).

Werner et al., "Air-suspension particle coating in the food industry: Part I—state of the art", Powder Technology, vol. 171, pp. 25-33 (2007).

* cited by examiner

VITAMIN DELIVERY PARTICLE

CROSS-REFERENCE TO RELATED APPLICATIONS

This application is a non-provisional of U.S. Provisional Patent Application Ser. No. 62/650,038, filed Mar. 29, 2018, the contents of which are incorporated by reference herein in their entireties.

BACKGROUND OF THE INVENTION

Field of Invention

This invention relates to controlled release compositions, encapsulation compositions and methods for making and using them.

Description of Related Art

There are many microencapsulated delivery systems disclosed in the art to control the oxidative stability, and release profile oil soluble vitamins. Such systems have previously suffered from a number of drawbacks.

Matrix microcapsules that provide release of vitamin upon ingestion, in the stomach, in the small or large intestines generally lose a cumulative amount of more than 50% of the encapsulated vitamin active during a combination of one or more of the following: the manufacturing process; the storage of the encapsulated vitamin powder under uncontrolled temperature and humidity conditions; incorporation of the vitamin powder into finished product forms that have various other minerals, metals, and other vitamins; transport, distribution, and storage of the finished product in the supply chain; intermittent exposure of the finished product to conditions that lead to oxidative damage of the vitamin Such vitamin controlled release systems are made using a combination of polysaccharides, antoxidants, vegetable oils, and emulsifiers. Such a combination is generally spray dried to form a powder, and this powder is generally utilized in premixes that are then incorporated into finished product formulations, such as vitamin supplements or other vitamin delivery product forms.

Polysaccharide based controlled release systems generally dissolve in water; therefore, such controlled release systems are ideal for anhydrous formulations, or formulation with low free water. Such formulations also would begin to break down upon ingestion, and perhaps would degrade prior to reaching the intestine, where absorption of such vitamins is ideal. Polymers that are used to develop a membrane around the vitamin active material could be crosslinked to provide a sufficient barrier to retain the encapsulated active until its desired release. However, the crosslinking reduces the degradability of such materials in the body and in the environment.

When polysaccharide-based microcapsules containing vitamin actives are incorporated into anhydrous product forms, these materials must be kept in controlled conditions of humidity, temperature, light, and oxygen concentration. The polysaccharide membranes provide acceptable stability to oxygen, but not to the various other insults that lead to oxidative degradation. For example, when these encapsulated vitamins are formulated with minerals, metals, and other vitamins, the combination of oxygen, moisture, divalent metal ions, heat, and light results in significant degradation of the vitamin active, despite its encapsulation in a polysaccharide matrix. The incorporation of anti-oxidants into the encapsulation formulation can help prolong oxidative degradation, but cannot manage degradation due to moisture.

In order to deliver a consumer noticeable benefit, yet deliver that benefit at a low cost, encapsulation is used to isolate a vitamin active from the non-encapsulated vitamin or mineral that is incorporated into the formulation. The invention allows one to encapsulate a single vitamin, or combination of vitamins, to incorporate into the composition, and achieve vitamin survivability through the supply chain.

The inventors have found that modifying the core composition and the surrounding wall material composition can significantly reduce the degradation of vitamins. The incorporation of wax materials protects the vitamin against moisture and oxygen diffusion. Cross-linking the polysaccharide improves protection against moisture and oxygen. Zein is a material that protects well against both, but not under all stressed stability conditions. The inventors have found that mannitol, methyl cellulose, carboxymethyl cellulose, and carboxymethyl chitosan protect well against oxygen, but provide lesser protection from moisture.

Accordingly, it is desired to provide a free flowing powder that can reduce the degradation of vitamins, especially in formulations containing divalent metal ions, humid environments, and oxygen rich environments. It is further desired to provide a formulation in which encapsulated vitamins remain stable during the dehydration process, during the incorporation of the encapsulated active with other minerals, and/or during the transport, storage and distribution of the formulation comprising the encapsulated active.

All references cited herein are incorporated herein by reference in their entireties. The citation of any reference is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

BRIEF SUMMARY OF THE INVENTION

Accordingly, a first aspect of the invention comprises controlled release particles comprising: (a) a core comprising at least one vitamin which is oil-soluble or oil-dispersible; and (b) a wall at least partially surrounding the core, wherein the controlled release particles are produced by reacting (i) a first composition comprising a hydrophobic oil, the at least one vitamin, an anti-oxidant and a wax with (ii) a second composition comprising a water soluble emulsifier, a corn protein and a solvent to form an intermediate product, which is mixed with (iii) a third composition comprising a cellulosic polymer in water, and dehydrated to provide the controlled release particles.

In certain embodiments, the controlled release particles comprise 1.9-22 wt. % of an oil soluble or oil dispersible vitamin, 3-37% wt. % of a hydrophobic oil, 1.8-22% wt. % of an anti-oxidant, 4.6-55.4 wt. % of a corn protein, 1-3.15 wt. % of a cellulosic polymer, 0-11 wt. % of a wax, 0-4 wt. % of a silica flow aid, optionally 1-11.5 wt. % of a polysaccharide, and optionally 0-0.4% pea protein, wherein the controlled release particles are anhydrous and the oil soluble vitamin is encapsulated in a polymer matrix effective to retain the oil soluble vitamin activity upon exposure to water, oxygen, light, and heat.

In certain embodiments, the controlled release particles comprise 4-30 wt. % of an oil soluble or oil dispersible vitamin, 7-60% wt. % of a hydrophobic oil, 0.6-4.4 wt. % of an anti-oxidant, 3-21.7 wt. % of a corn protein, 1.7-4 wt. % of an oil soluble emulsifier, 14-40 wt. % of a polysaccharide, 1-9.4 wt. % of a wax, 1-9.4 wt. % of a silica flow aid, optionally 0-3 wt. % of a cellulosic polymer, and optionally 0.6-3 wt. % of a water soluble antioxidant, wherein the controlled release particles are anhydrous and the oil soluble vitamin is encapsulated in a polymer matrix effective to retain the oil soluble vitamin activity upon exposure to water, oxygen, light and heat.

In certain embodiments, the oil soluble vitamin is a member selected from the group consisting of fat-soluble vitamin-active materials, pro vitamins and pure or substantially pure vitamins, both natural and synthetic, or chemical derivatives thereof, crude extractions containing such substances, vitamin A, vitamin D, and vitamin E active materials as well as vitamin K, carotene and the like, or mixtures of such materials. The oil-soluble vitamin oil concentrate may be a high potency fish liver oil containing vitamin A and/or D, a synthetic vitamin A palmitate and/or acetate concentrated in an oil solution, vitamin D, or D either concentrated in oil solution or as an oleaginous resin, vitamin E (d-alpha tocopheryl acetate) in an oil solution, or vitamin K in oil solution, or beta-carotene as a crystalline oil suspension in oil.

In certain embodiments, the hydrophobic oil is a member selected from the group consisting of a flavorant, an essential oil, a sweetener, an active pharmaceutical ingredient, a vitamin oil, a vegetable oil, a triglyceride.

In certain embodiments, the hydrophobic oil is a mixture of a hydrophobic active ingredient and a diluent. The diluent is used to change the properties of the hydrophobic material, for example, the polarity, the melting point, the surface tension, the viscosity, the density, or the volatility of the hydrophobic active. In certain embodiments, the diluent is a member selected from plant waxes, animal waxes, petroleum based waxes, synthetic waxes, mineral waxes, brominated oils, hydrophobically modified inorganic particles, nonionic emulsifiers, oil thickening agents.

In certain embodiments, the polysaccharide is a member selected from the group consisting of octenyl succinic acid anhydride modified starch, gum arabic, xanthan gum, gellan gum, pectin gum, konjac gum and carboxyalkyl cellulose.

In certain embodiments, the anti-oxidant is a member selected from the group consisting of vitamins, phytochemicals, and enzymes. Examples of vitamins having antioxidant properties are Vitamin A, Vitamin C, Vitamin E, folic acid, (Beta-carotene), Coenzyme Q10, alpha-tocopherol. Examples of phytochemicals having antioxidant properties include Carotenoids, flavonoid, allyl sulfides, polyphenols. Examples of enzymes that can be used as antioxidants are Superoxide dismutase, glutathione peroxidase, glutathione reductase, catalase.

In certain embodiments, the corn protein is water soluble, salt soluble, alkali soluble, or alcohol soluble. Albumins are water soluble, Globulins are salt soluble. Glutelin are alkali soluble. Zeins are prolamines that are alcohol soluble. Preferred corn proteins are Alpha (α-zein) with a molecular weight of 21-25 kD, Beta (β-zein), molecular weight of 17-18 kD, Delta (δ-zein), molecular weight of 9-12 kD, which is often coextracted with α-zein because of its immunological relationship to α-zein, Gamma (γ-zein), 26-29 kD.

In certain embodiments, the cellulosic polymer is a member selected from the group consisting of naturally derived polymers that have a solubility in water greater than 1 wt. %, with a cellulose backbone including, but not limited to, cellulose esters and cellulose ethers. Cellulose esters include cellulose acetate, cellulose acetate-propionate, cellulose acetate butyrate. Cellulose ethers include ethyl cellulose, methyl cellulose, hydroxymethyl cellulose, hydroxyethyl cellulose, hydroxypropyl cellulose, carboxymethyl cellulose, and their salts. For example,

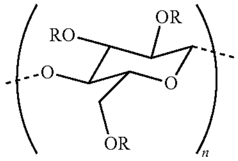

where R=H, $CH_2CH(OH)CH_3$, $CH_3$, $CH_2CO_2H$, $CH_2CH_3$ (Hydroxymethyl, methyl, hydroxypropyl, methyl, etc.).

In certain embodiments, the silica flow aid is a member selected from the group consisting of fumed silica, precipitated silica, calcium silicate, aluminosilicate, and combinations thereof.

In certain embodiments, the controlled release particles have a diameter from 0.1 microns to less than 100 microns.

In certain embodiments, the controlled release particles have an Environmental Degradability index greater than 80.

In certain embodiments, the hydrophobic oil ingredient comprises a mixture of a hydrophobic active and a material selected from the group consisting of plant waxes, animal waxes, petroleum based waxes, synthetic waxes, mineral waxes, brominated oils, hydrophobically modified inorganic particles, nonionic emulsifiers and oil thickening agents.

A second aspect of the invention comprises a composition comprising the controlled release particles of the invention, wherein the composition is a powdered food product, a fluid food product, a powdered nutritional supplement, a fluid nutritional supplement, a fluid fabric enhancer, a solid fabric enhancer, a fluid shampoo, a solid shampoo, hair conditioner, body wash, solid antiperspirant, fluid antiperspirant, solid deodorant, fluid deodorant, fluid detergent, solid detergent, a diaper, a nutraceutical supplement, a skin care product, a baby care product, a family care product, a feminine care product, a household care product.

In certain embodiments, the composition further comprises at least one suspension agent to suspend the controlled release particles, wherein the at least one suspension agent is at least one member selected from the group consisting of a rheology modifier, a structurant and a thickener.

In certain embodiments of the composition, the at least one suspension agent has a high shear viscosity at, 20 $sec^{-1}$ shear rate and at 21° C., of from 1 to 7000 cps and a low shear viscosity, at 0.5 $sec^{-1}$ shear rate at 21° C., of greater than 1000 cps.

In certain embodiments, the composition has a high shear viscosity, at 20 $sec^{-1}$ and at 21° C., of from 50 to 3000 cps and a low shear viscosity, at 0.5 $sec^{-1}$ shear rate at 21° C., of greater than 1000 cps.

In certain embodiments of the composition, the at least one suspension agent is selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

In certain embodiments, the composition has at least two controlled release technologies, which release different hydrophobic oil compositions and are selected from the group consisting of neat oils, friction-triggered release microcapsules and water-triggered release microcapsules.

A third aspect of the invention comprises a method for preparing the controlled release particles of the invention, said method comprising: (a) preparing a first composition by mixing the hydrophobic active with oil and raising the temperature to the melting temperature of the active under a blanket of inert gas; (b) adding anti-oxidants or wax to the first composition; (c) preparing a second composition by dissolving the corn protein in a suitable solvent (for example, zein corn protein can be dissolved in ethanol, propylene glycol, or glycerol at a temperature of 140° C.-150° C.); (d) emulsifying the first composition in the second composition with agitation sufficient to achieve a desired particle size of dispersed particles in a dispersed phase of a resulting emulsion, wherein a pea protein isolate is optionally incorporated into the emulsion to control a particle size distribution; (e) precipitating the corn protein onto an oil phase of the emulsion to form a shell, wherein the corn protein is precipitated by: (i) lowering a temperature of the emulsion below a corn protein dissolution temperature while stirring the emulsion, at such a rate that the corn protein precipitates onto the oil phase of the emulsion to form the shell, or (ii) adding water and reducing the temperature at a rate that causes controlled precipitation of the corn protein onto the oil phase of the emulsion to form the shell; (f) separating the dispersed particles from the liquid suspension; (g) optionally, adding pea protein or water to cause further aggregation of the particles; (h) resuspending the particles in mixture of a third composition comprising a cellulosic polymer and water to create a spray-ready suspension; (i) optionally, adding polysaccharide and flow aid to the suspension as process aids to help form particles; (j) spray drying the spray-ready emulsion to provide a powder; and (k) adding a silica flow aid to the powder to provide a modified powder.

A fourth aspect of the invention comprises a method for preparing the controlled release particles of the invention, said method comprising: (a) preparing the first composition by mixing a hydrophobic active with oil, raising the temperature to a melting temperature of the hydrophobic active under a blanket of inert gas and adding the anti-oxidant, the wax and the oil soluble emulsifier; (b) preparing the second composition by dissolving the corn protein and the water soluble emulsifier in the solvent; (c) emulsifying the first composition in the second composition with agitation sufficient to achieve a desired particle size of dispersed particles in a dispersed phase of a resulting emulsion, wherein a fumed silica is optionally incorporated into the emulsion to control a particle size distribution; (d) precipitating the corn protein onto an oil phase of the emulsion to form a shell, wherein the corn protein is precipitated by: (i) lowering a temperature of the emulsion below a corn protein dissolution temperature while stirring the emulsion, at such a rate that the corn protein precipitates onto the oil phase of the emulsion to form the shell, or (ii) adding an aqueous solution of polysaccharide that causes controlled precipitation of the corn protein onto the oil phase of the emulsion to form the shell; (e) optionally, resuspending the dispersed particles in the third composition comprising the cellulosic polymer and water to create a spray-ready suspension; (f) optionally, adding fumed silica to the suspension as a process aid to help form particles during spray drying; (g) optionally spray drying the spray-ready suspension to provide a powder; and (h) adding a silica flow aid to the powder to provide a modified powder.

BRIEF DESCRIPTION OF SEVERAL VIEWS OF THE DRAWINGS

The invention will be described in conjunction with the following drawings, wherein.

DETAILED DESCRIPTION OF PREFERRED EMBODIMENTS OF THE INVENTION

Glossary

Figure 1A:
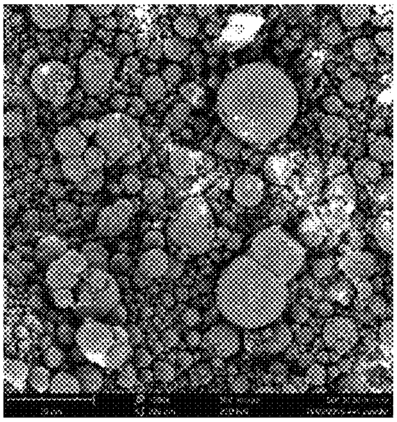
FIG. 1A is a 1200× magnification image of an embodiment of a starch encapsulated vitamin of the invention wherein a matrix particle has oil/vitamin cores.
Figure 1B:
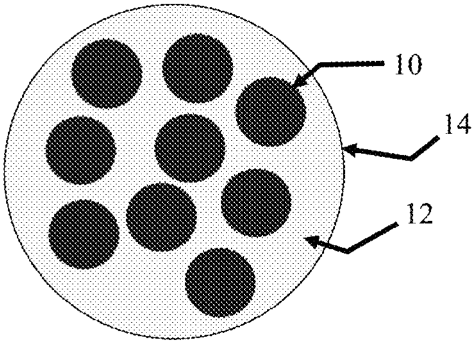
FIG. 1B is a schematic illustration of the embodiment of FIG. 1A, showing the oil/vitamin core 10 surrounded by a matrix of starch polymer 12. The starch polymer forms a wall 14 around the oil/vitamin cores.
Figure 2A:
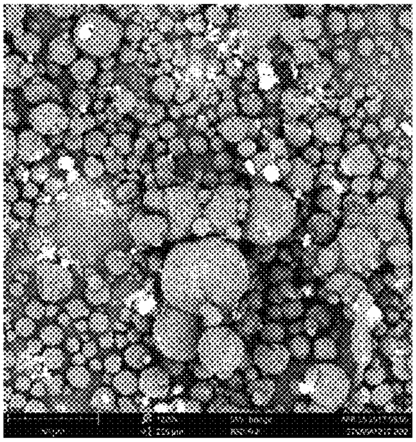
FIG. 2A is a 1200× magnification image of an embodiment of the starch encapsulated vitamin of the invention having wax in the core particles (wax inside, starch matrix outside).
Figure 2B:
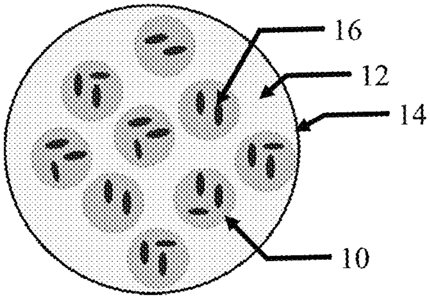
FIG. 2B is a schematic illustration of the embodiment of FIG. 2A showing vitamin material 16 suspended in oil/wax cores 10. In turn, the oil/wax cores are surrounded by a continuous starch matrix 12 that forms a wall 14 around the encapsulated oil/vitamin.
Figure 2C:
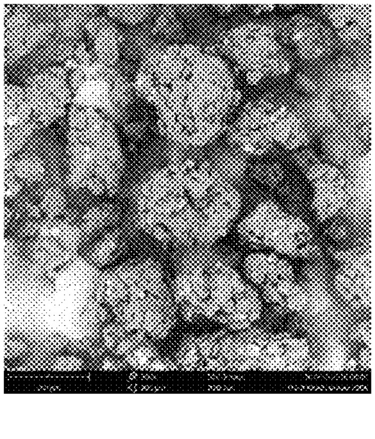
FIG. 2C is a 300× magnification image of an embodiment of the starch encapsulated vitamin of the invention having wax on the surface of the starch particles.
Figure 2D:
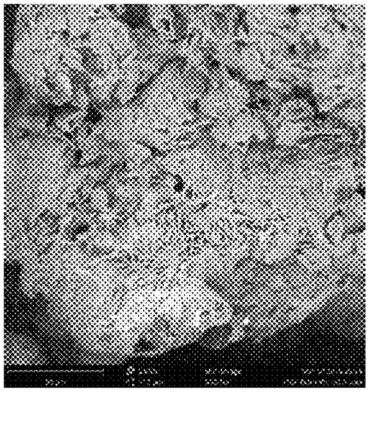
FIG. 2D is a 2100× magnification image of the embodiment of FIG. 2C.
Figure 3A:
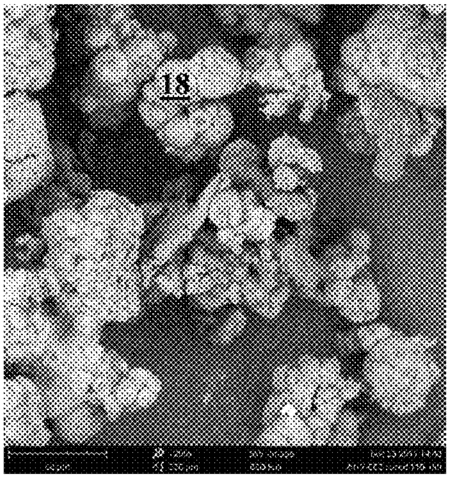
FIGS. 3A and 3B are 1200× magnification images of an embodiment of the starch encapsulated vitamin of the invention having a crosslinked polysaccharide matrix surrounding multiple cores.
Figure 3B:
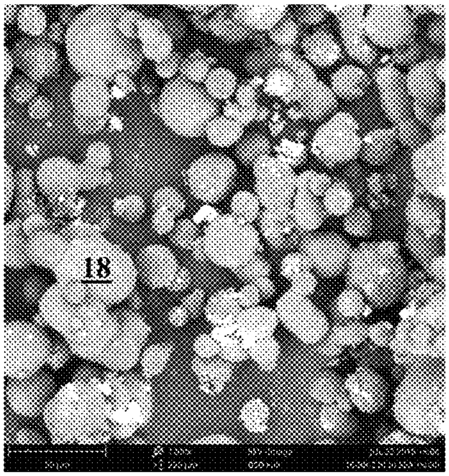
Figure 4A:
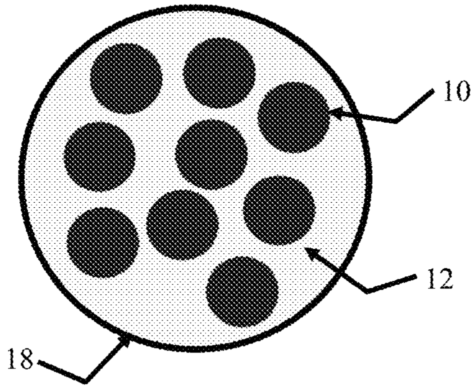
FIG. 4A is a schematic illustration of an embodiment of a dual coated microparticle of the invention showing oil/vitamin core 10 surrounded by a starch matrix 12 that has been crosslinked to create a water insoluble shell 18.
Figure 4B:
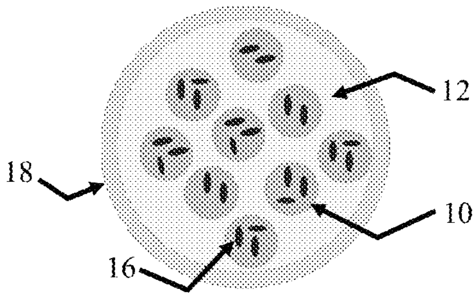
FIG. 4B is a is a schematic illustration of another embodiment of a dual coated microparticle of the invention showing vitamin material 16 suspended in oil/wax cores 10. In turn, the oil/wax cores are surrounded by a continuous starch matrix 12 that has been crosslinked to create a water insoluble shell 18.
Figure 4C:
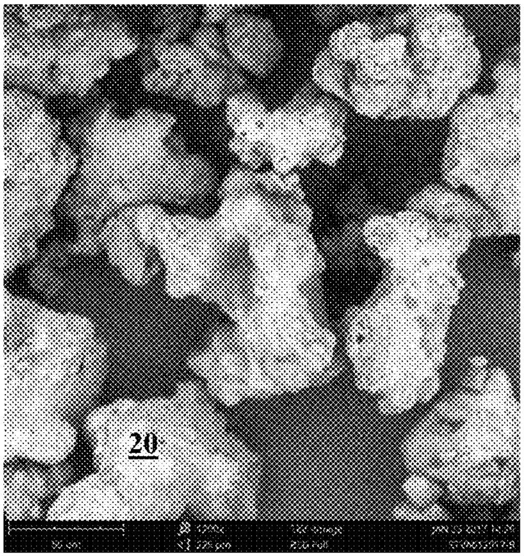
FIG. 4C is a 1200× magnification image of an embodiment of a dual coated microparticle of the invention having mannitol as a second shell 20.
Figure 4D:
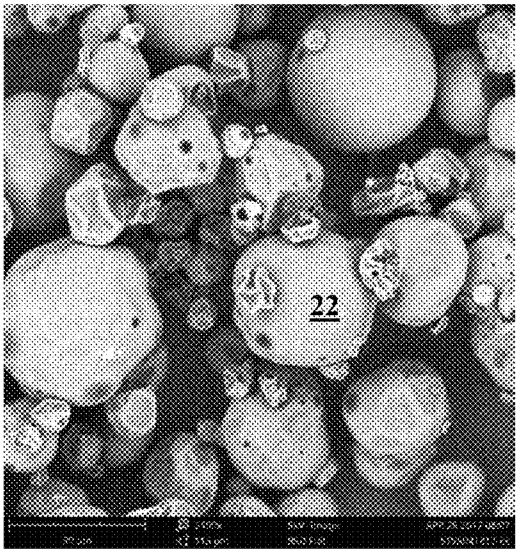
FIG. 4D is a 1200× magnification image of an embodiment of a dual coated microparticle of the invention having methocel as a second shell 22.
Figure 5A:
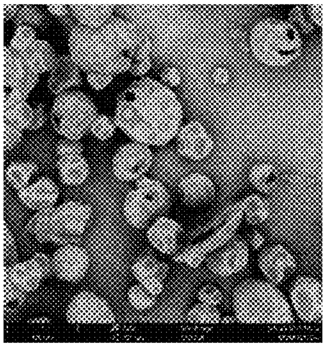
FIG. 5A is a 500× magnification image of an embodiment of a microparticle of the invention having enhanced oxygen and water barrier properties.
Figure 5B:
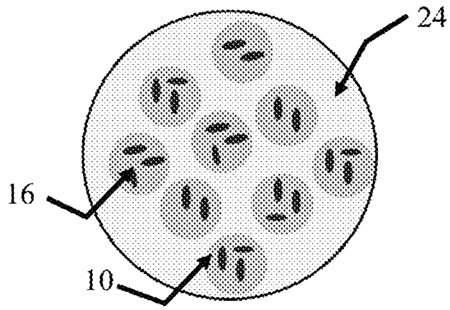
FIG. 5B is a schematic illustration of the embodiment of FIG. 5A showing vitamin material 16 suspended in oil/wax core 10. These oil/wax cores are entrapped by a continuous zein corn protein layer 24.
Figure 6A:
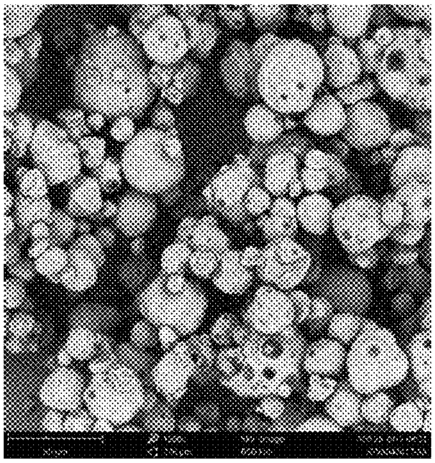
FIG. 6A is a 1200× magnification image of an embodiment of a microparticle of the invention having a second coating of methyl cellulose.
Figure 6B:
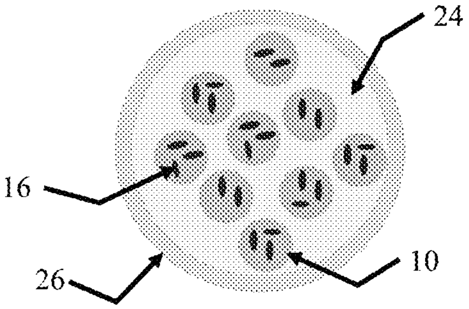
FIG. 6B is a schematic illustration of the embodiment of FIG. 6A showing vitamin material 16 suspended in oil/wax core 10. The oil/wax cores are entrapped by a continuous zein corn protein layer 24, and then the particle is coated with a methyl cellulose layer 26.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from the group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, unless otherwise noted, "alkyl" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups, the alkyl groups may be the same or different.

The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like.

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

Particles

The invention addresses one or more of the prior art deficiencies described above by providing controlled release particles. The particles are particularly well-suited for use in encapsulation of hydrophobic, nonpolar materials.

In one embodiment is provided a population of low permeability controlled release particles comprising: (a) a core comprising at least one vitamin which is oil-soluble or oil-dispersible; and (b) a wall at least partially surrounding the core, wherein the controlled release particles are produced by reacting (i) a first composition comprising a hydrophobic oil, the at least one vitamin, an anti-oxidant and a wax with (ii) a second composition comprising a water soluble emulsifier, a corn protein and a solvent to form an intermediate product, which is mixed with (iii) a third composition comprising a cellulosic polymer in water, and dehydrated to provide the controlled release particles.

In certain embodiments, such controlled release particles preferably comprise 1.9-22 wt. % of an oil soluble or oil dispersible vitamin, 3-37% wt. % of a hydrophobic oil, 1.8-22% wt. % of an anti-oxidant, 4.6-55.4 wt. % of a corn protein, 1-3.15 wt. % of a cellulosic polymer, 0-11% wax, 0-4 wt. % of a silica flow aid, optionally 1-11.5 wt. % of a polysaccharide, optionally 0-0.4% pea protein, wherein the controlled release particles are anhydrous and the oil soluble vitamin is encapsulated in a polymer matrix effective to retain the oil soluble vitamin activity upon exposure to water, oxygen, light, and heat.

In certain other embodiments, such controlled release particles comprise 4-30 wt. % of an oil soluble or oil dispersible vitamin, 7-60% wt. % of a hydrophobic oil, 0.6-4.4% wt. % of an anti-oxidant, 3-21.7 wt. % of a corn protein, 1.7-4% of an oil soluble emulsifier, 14-40 wt. % of a polysaccharide, 1-9.4 wt. % of a wax, 1-9.4 wt. % of a silica flow aid, optionally 0-3 wt. % of a cellulosic polymer, and optionally 0.6-3% of a water soluble antioxidant, wherein the controlled release particles are anhydrous and the oil soluble vitamin is encapsulated in a polymer matrix effective to retain the oil soluble vitamin activity upon exposure to water, oxygen, light, and heat.

The oil soluble or oil dispersible vitamin active ingredient is a substance that is active (or effective) to provide a desired effect, alone or in combination with other substances and/or conditions. It is present in the particles in an amount effective to provide a desired effect. The amount can be, e.g., from 1.8 wt. % or 6 wt. % or 8 wt. % to 15 wt. % or 18 wt. % or 22 wt. % or 30 wt. %.

The oil soluble vitamins include but are not limited to fat-soluble vitamin-active materials, pro vitamins and pure or substantially pure vitamins, both natural and synthetic, or chemical derivatives thereof, crude extractions containing such substances, vitamin A, vitamin D, and vitamin E active materials as well as vitamin K, carotene and the like, or mixtures of such materials. The oil-soluble vitamin oil concentrate may be a high potency fish liver oil containing vitamin A and/or D, a synthetic vitamin A palmitate and/or acetate concentrated in an oil solution, vitamin D, or D either concentrated in oil solution or as an oleaginous resin, vitamin E (d-alpha tocopheryl acetate) in an oil solution, or vitamin K in oil solution, or beta-carotene as a crystalline oil suspension in oil. Suitable vegetable oils include but are not limited to oils derived from palm, corn, canola, sunflower, safflower, rapeseed, castor, olivek, soybean, coconut and the like in both the unsaturated forms and hydrogenated forms, and mixtures thereof.

The hydrophobic oil is a member selected from the group consisting of a flavorant, an essential oil, a sweetener, an active pharmaceutical ingredient, a vitamin oil, a vegetable oil, a triglyceride. It is present in the particles in an amount effective to stabilize the vitamin material. The amount can be, e.g. from 3 wt. % or 10 wt. % or 13 wt. % to 25 wt. % or 30 wt. % or 37 wt. % or 60 wt. %.

Suitable flavorants include but are not limited to oils derived from plants and fruits such as citrus oils, fruit essences, peppermint oil, clove oil, oil of wintergreen, anise, lemon oil, apple essence, and the like. Artificial flavoring components are also contemplated. Those skilled in the art will recognize that natural and artificial flavoring agents may be combined in any sensorially acceptable blend. All such flavors and flavor blends are contemplated by this invention. Carriers may also be mixed with flavors to reduce the intensity, or better solubilize the materials. Carriers such as vegetable oils, hydrogenated oils, triethyl citrate, and the like are also contemplated by the invention.

Suitable essential oils include but are not limited to those obtained from thyme, lemongrass, citrus, anise, clove, aniseed, roses, lavender, citronella, eucalyptus, peppermint, camphor, sandalwood, cinnamon leaf and cedar. Essential oils that exhibit antimicrobial properties are also contemplated by this invention.

Suitable sweeteners include but are not limited to materials that contain varying amounts of disaccharide and/or fructose; erythritol, honey, and/or evaporated cane juice; and rebaudioside A, and the like Suitable active pharmaceutical ingredients include but are not limited to water insoluble materials that have a melting point below 50° C.

Suitable triglycerides include but are not limited to those disclosed in U.S. Pat. No. 6,248,909B1.

Suitable hydrocarbons that can be the active or can be used in combination with the active in order to change the physical or chemical properties of the active, include but are not limited to, waxes, density modifiers, surface tension modifiers, melting point modifiers, viscosity modifiers, and mixtures thereof. Examples include animal waxes such as beeswax, plant waxes such as carnauba wax, candelilla wax, bayberry wax, castor wax, tallow tree wax, soya wax, rice bran wax, hydrogenated rice bran wax, soya wax, hydrogenated soya wax, hydrogenated vegetable oil. Examples of petroleum derived waxes are paraffin waxes and microcrystalline waxes. An example of synthetic wax is polyethylene wax. Examples of materials that can modify the density of the active phase in the particle are brominated vegetable oil, nanoclays such as montmorrilonite or kaolin, hydrophobically modified clays, hydrophobically modified precipitated silicas or fumed silicas. Examples of materials that can alter the surface tension of the active phase in the particle are nonionic emulsifiers such as polysorbate-type nonionic surfactant (e.g. Tween™), alcohol ethoyxlate based surfactants (e.g. Genapol™). Examples of oil thickening agents are waxes mentioned above, modified organopolysiloxanes, silicone gums, hydrogenated castor oil, paraffin oils, polyolefins, and the like. The amount of wax material can be, e.g., from 0.9 wt. %, or 3 wt. %, or 3.9 wt. %, or 7.5 wt. %, or 9 wt. %, or 11 wt. %.

The polysaccharide is present in the particles in an amount effective to provide a coating and/or matrix having the desired structural properties. The amount can be, e.g., from 1 wt. % or 3 wt. % or 4.6 wt. % or 8.4 wt. % to 9 wt. % or 11 wt. % or 14 wt. % or 40 wt. %.

Polysaccharides having emulsifying and emulsion stabilizing capacity are preferred. The polysaccharide is preferably a member selected from the group consisting of octenyl succinic acid anhydride modified starch, gum arabic, xanthan gum, gellan gum, pectin gum, konjac gum and carboxyalkyl cellulose.

The corn protein is present in the particles of the invention in an amount effective to provide the particles with desired water insolubility properties. The amount can be, e.g., from 4.6 wt. % or 15 wt. % or 22 wt. % or 40 wt. % to 45 wt. % or 55 wt. %.

The corn protein is preferably a member selected from the group consisting of water soluble, salt soluble, alkali soluble, or alcohol soluble. Albumins are water soluble, Globulins are salt soluble. Glutelin are alkali soluble. Zeins are prolamines that are alcohol soluble. Preferred corn proteins are Alpha ($\alpha$-zein) with a molecular weight of 21-25 kD, Beta ($\beta$-zein), molecular weight of 17-18 kD, Delta ($\delta$-zein), molecular weight of 9-12 kD, which is often coextracted with $\alpha$-zein because of its immunological relationship to $\alpha$-zein, Gamma ($\gamma$-zein), 26-29 kD.

The anti-oxidant is present in the particles of the invention in an amount effective to retard oxidative degradation of the vitamin during the particle making process. The amount can be, e.g. 1.8 wt. %, or 4.4 wt. %, or 6 wt. %, or 7.8 wt. %, or 15 wt. %, or 18 wt. %, or 22 wt. %.

The anti-oxidant is preferably a member selected from the group consisting of vitamins, phytochemicals, and enzymes. Examples of vitamins having antioxidant properties are Vitamin A, Vitamin C, Vitamin E, folic acid, (Beta-carotene), Coenzyme Q10, alpha-tocopherol. Examples of phytochemicals having antioxidant properties include Carotenoids, flavonoid, allyl sulfides, polyphenols. Examples of enzymes that can be used as antioxidants are Superoxide dismutase, glutathione peroxidase, glutathione reductase, catalase. Water soluble antioxidants include grapeseed extract, ascorbic acid, citric acid, and the like.

The oil soluble emulsifier is present in the particles of the invention in an amount effective to maintain a stable emulsion during the particle making process. The amount can be, e.g., 1.7 wt. %, or 2.2 wt. %, or 2.8 wt. %, or 4 wt. %, or 10 wt. %, or 15 wt. %.

The oil soluble emulsifier is preferably a member selected from the group consisting of nonionic surfactants and phospholipids. Nonionic emulsifiers are selected from polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, sorbitan esters, monoglycerides. Phospholipids are preferably selected from lecithins, preferably fluid, deoiled, or fractionated lecithins. Preferred lecithins have greater than 20% by weight of phosphatidylcholine.

The cellulosic polymer is present in the particles of the invention in an amount effective to provide the particles with desired durability and moisture protection properties. The amount can be, e.g., from 1.3 wt. % or 4 wt. % or 6 wt. % or 11 wt. % to 12.3 wt. % or 15 wt. %.

The cellulosic polymer is preferably a member selected from the group consisting of naturally derived polymers that have a solubility in water greater than 1 wt. %, with a cellulose backbone including, but not limited to, cellulose esters and cellulose ethers. Cellulase esters include cellulose acetate, cellulose acetate-propionate, cellulose acetate butyrate. Cellulose ethers include ethyl cellulose, methyl cellulose, hydroxymethyl cellulose, hydeoxyethyl cellulose, hydroxypropyl cellulose, carboxymethyl cellulose, and their salts. For example,

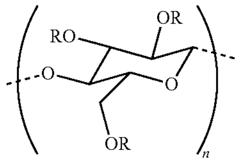

where R═H, $CH_2CH(OH)CH_3$, $CH_3$, $CH_2CO_2H$, $CH_2CH_3$ (Hydroxymethyl, methyl, hydroxypropyl, methyl, etc.).

The silica flow aid is present in the particles in an amount effective to minimize or eliminate clumping during both capsule formation and spray drying. The amount can be, e.g., from 0.3 wt. % or 1 wt. % or 1.6 wt. % or 3 wt. % to 3.3 wt. % or 4 wt. % or 7.5 wt. % or 10 wt. %.

The silica flow aid is preferably a precipitated silica and more preferably a fumed silica. Hydrophobic silicas are preferred. Silicas that have a surface area greater than 60 $m^2/g$ are more preferred. Preferred fumed silicas include AEROSIL R 812, SIPERNAT D10 and SIPERNAT D17. Hydrophilic fumed silicas are preferred as process aids. Preferred fumed silicas include Aerosil 200F. Preferred precipitated silicas include SYLOID 244, which is hydrophobic and ZEOTHIX, which is hydrophilic. Alternatively, the silica flow aid comprises calcium silicate, such as Hubersorb 250 or 600 grades sold by Huber Corporation. Alternatively, the silica flow aid is an aluminosilicate such as the Zeolex grades sold by Huber Corporation.

The controlled release particles are preferably spherical but non-spherical shapes are also within the scope of the invention. The particles preferably have a diameter from 0.05-250 microns, or from 0.1 microns to less than 100 microns.

Method of Making the Particles

Figure 7A:
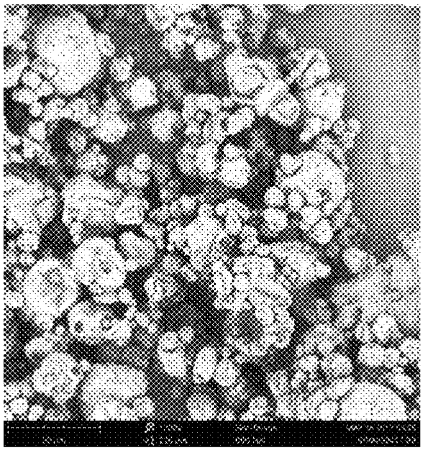
FIG. 7A is a 1200× magnification image of an embodiment of a microparticle of the invention having Aqua Zein capsules with methyl cellulose coating.
Figure 7B:
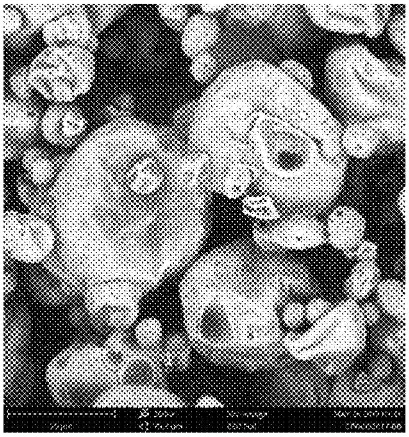
FIG. 7B is a 3600× magnification image of the embodiment of FIG. 7A.
Figure 7C:
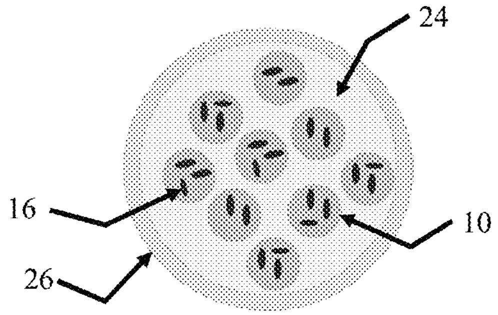
FIG. 7C is a schematic illustration of the embodiment of FIG. 7A.
Figure 8:
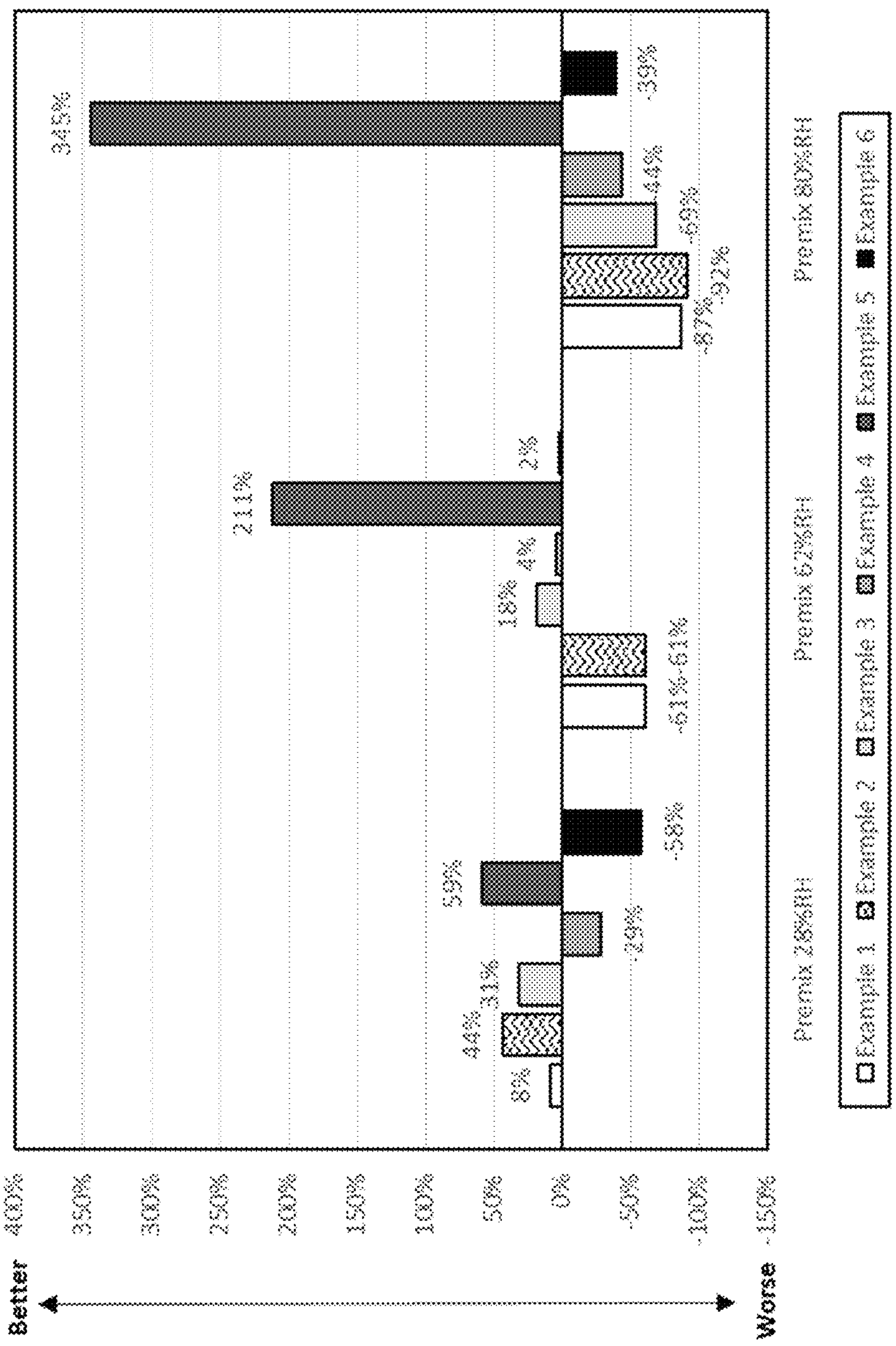
FIG. 8 is a beta-Carotene stability graph.
Figure 9:
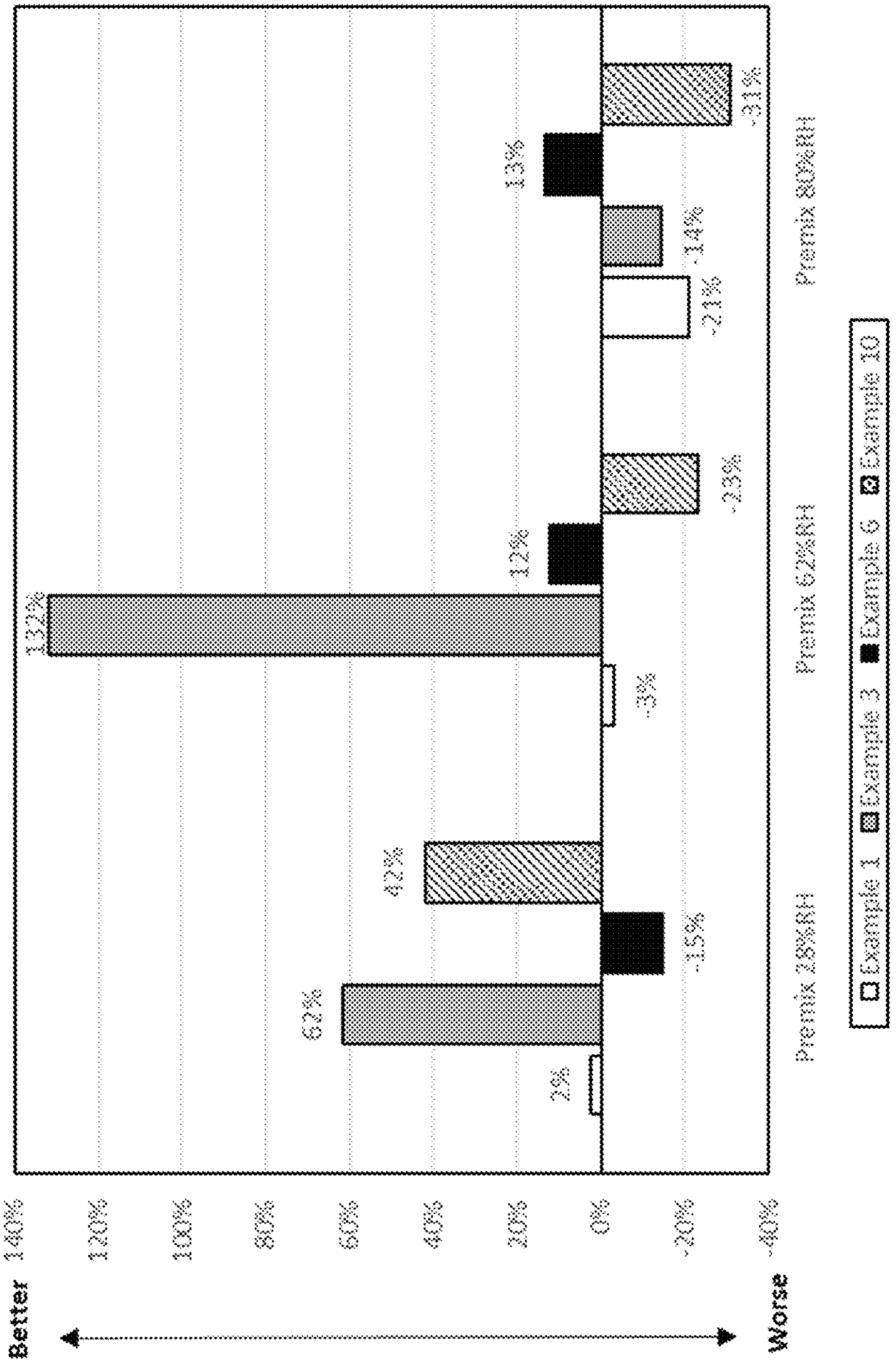
FIG. 9 is a Vitamin A Palmitate stability graph.

Referring to FIG. 7C, the particles of the invention are provided by a method comprising: (a) preparing a first composition by mixing the hydrophobic active with oil and raising the temperature to the melting temperature of the active under a blanket of inert gas; (b) adding anti-oxidants or wax to the first composition; (c) preparing a second composition by dissolving the corn protein in a suitable solvent (for example, zein corn protein can be dissolved in ethanol, propylene glycol, or glycerol at a temperature of 140° C.-150° C.); (d) emulsifying the first composition in the second composition with agitation sufficient to achieve a desired particle size of dispersed vitamin particles 16 surrounded by oil/wax 10, in a dispersed phase of a resulting emulsion, wherein a pea protein isolate is optionally incorporated into the emulsion to control a particle size distribution of oil/wax cores 10; (e) precipitating the corn protein onto an oil phase of the emulsion to form a continuous shell 24, wherein the corn protein is precipitated by: (i) lowering a temperature of the emulsion below a corn protein dissolution temperature while stirring the emulsion, at such a rate that the corn protein precipitates onto the oil phase of the emulsion to form the shell, or (ii) adding water and reducing the temperature at a rate that causes controlled precipitation of the corn protein onto the oil phase of the emulsion to form the shell 24; (f) separating the dispersed particles from the liquid suspension; (g) optionally, adding pea protein or water to cause further aggregation of the particles; (h) resuspending the particles in mixture of a third composition comprising a cellulosic polymer and water to create a spray-ready suspension; (i) optionally, adding polysaccharide and flow aid to the suspension as process aids to help form particles; (j) spray drying the spray-ready emulsion to provide a powder with a second coating 26; and (k) adding a silica flow aid to the powder to provide a modified powder.

Alternatively, the particles of the invention are prepared by a method comprising: (a) preparing the first composition by mixing a hydrophobic active with oil, raising the temperature to a melting temperature of the hydrophobic active under a blanket of inert gas and adding the anti-oxidant, the wax and the oil soluble emulsifier; (b) preparing the second composition by dissolving the corn protein and the water soluble emulsifier in the solvent; (c) emulsifying the first composition in the second composition with agitation sufficient to achieve a desired particle size of dispersed particles in a dispersed phase of a resulting emulsion, wherein a fumed silica is optionally incorporated into the emulsion to control a particle size distribution; (d) precipitating the corn protein onto an oil phase of the emulsion to form a shell, wherein the corn protein is precipitated by: (i) lowering a temperature of the emulsion below a corn protein dissolution temperature while stirring the emulsion, at such a rate that the corn protein precipitates onto the oil phase of the emulsion to form the shell, or (ii) adding an aqueous solution of polysaccharide that causes controlled precipitation of the corn protein onto the oil phase of the emulsion to form the shell; (e) optionally, resuspending the dispersed particles in the third composition comprising the cellulosic polymer and water to create a spray-ready suspension; (f) optionally, adding fumed silica to the suspension as a process aid to help form particles during spray drying; (g) optionally spray drying the spray-ready suspension to provide a powder; and (h) adding a silica flow aid to the powder to provide a modified powder. In certain embodiments, the polysaccharide solution comprises a water soluble antioxidant such as grapeseed extract.

Spray drying of the emulsion is preferably conducted in a co-current spray dryer, at an inlet air temperature of 325 to 415° F. (163-213° C.), preferably from 355 to 385° F. (179-196° C.) and an outlet air temperature of 160 to 215° F. (71-101° C.), preferably from 175-195° F. (79-91° C.).

The silica flow aid is added to the dry powder to improve the flowability of the powder. Addition of the silica flow aid minimizes the agglomeration of particles during the curing process.

Advantages of at least some embodiments of the inventive method include:

a) The method is a one-pot process that achieves water insoluble particles in an anhydrous form.

b) The materials used are GRAS (generally recognized as safe). The environmental fate of these materials meets biodegradability criteria.

c) The inventive composition and method can be used in a variety of applications, including but not limited to foods, flavors, nutraceuticals, pharmaceuticals, household care, personal care and beauty care.

d) The invention can utilize a commercially available, relatively inexpensive spray drying technique to engineer the particle.

e) The invention yields a water insoluble, anhydrous particle that can encapsulate hydrophobic actives with reduced losses under stressed conditions, such as, e.g., elevated temperatures, elevated levels of moisture, elevated levels of oxygen and elevated levels of divalent metal ions.

f) The invention offers multiple release triggers to empty the encapsulated active from the controlled release particle due to a matrix morphology wherein a portion of the encapsulated active is released upon a release trigger.

Compositions Containing the Particles

The invention further comprises compositions comprising the controlled release particles. Such compositions include but are not limited to a powdered food product, a fluid food product, a powdered nutritional supplement, a fluid nutritional supplement, a fluid fabric enhancer, a solid fabric enhancer, a fluid shampoo, a solid shampoo, hair conditioner, body wash, solid antiperspirant, fluid antiperspirant, solid deodorant, fluid deodorant, fluid detergent, solid detergent, a diaper, a nutraceutical supplement, a skin care product, a baby care product, a family care product, a feminine care product, a household care product.

The fluid compositions preferably further comprise at least one suspension agent to suspend the controlled release particles, wherein the at least one suspension agent is at least one member selected from the group consisting of a rheology modifier, a structurant and a thickener.

The at least one suspension agent preferably has a high shear viscosity at, 20 $sec^{-1}$ shear rate and at 21° C., of from 1 to 7000 cps and a low shear viscosity, at 0.5 $sec^{-1}$ shear rate and at 21° C., of greater than 1000 cps or 1000-200,000 cps. In certain embodiments, the composition has a high shear viscosity, at 20 $sec^{-1}$ and at 21° C., of from 50 to 3000 cps and a low shear viscosity, at 0.5 $sec^{-1}$ shear rate and at 21° C., of greater than 1000 cps or 1000-200,000 cps.

Preferably, the at least one suspension agent is selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

In certain embodiments, the composition has at least two controlled release technologies, which release different hydrophobic oil compositions and are selected from the group consisting of neat oils, friction-triggered release microcapsules and water-triggered release microcapsules.

The invention will be illustrated in more detail with reference to the following Examples, but it should be understood that the present invention is not deemed to be limited thereto.

EXAMPLES

Materials and Methods

The following premix will be utilized in the stability testing data provided in the examples below.

| Nutrient (Ingredient Used) | Nutrient Levels |
|---|---|
| Vitamin B1 (as Thiamin Mononitrate) | 1.2 mg |
| Vitamin B2 (as Riboflavin) | 1.3 mg |
| Niacin (as Niacinamide) | 16 mg |
| Pantothenic Acid (as D-Calcium Pantothenate) | 5 mg |
| Vitamin B6 (as Pyridoxine) | 1.7 mg |
| Biotin (as D-Biotin PWD) | 30 mcg |
| Folic Acid (as Folic Acid PWD) | 240 mcg |
| Vitamin B12 (as Cyanocobalamin) | 2.4 mcg |
| Vitamin C (as Ascorbic Acid) | 90 mg |
| Vitamin D3 (as Cholecalciferol) | 800 IU |
| Vitamin E (as DL-α-Tocopheryl Acetate) | 11.2 IU |
| Vitamin K1 (as Phytonadione) | 120 mcg |
| Chromium (as Chromium Chloride 6H2O) | 35 mcg |
| Copper (as Copper Gluconate) | 0.9 mg |

-continued

| Nutrient (Ingredient Used) | Nutrient Levels |
|---|---|
| Iodine (as Potassium Iodide) | 150 mcg |
| Iron (as Ferrous Fumarate) | 18 mg |
| Manganese (as Manganese Sulfate 1H2O) | 2.3 mg |
| Molybdenum (as Sodium Molybdate 2H2O) | 45 mcg |
| Selenium (as Sodium Selenite) | 55 mcg |
| Zinc (as Zinc Sulfate 1H2O) | 11 mg |
| Calcium (as Dicalcium Phosphate Anhydrous) | 130 mg |
| Phosphorus (as Dicalcium Phosphate Anhydrous) | 100 mg |
| Magnesium (as Magnesium Oxide) | 42 mg |
| Croscarmellos Sodium | Q.S. |
| Microcrystalline Cellulose | Q.S. |

Thermal Gravimetric Analysis

A Thermal Gravimetric Analysis pan is exposed to a Bunsen burner to remove any residue from the pan. Approximately 5 milligrams of sample is weighed onto a pan of a Thermal Gravimetric Analyzer (Model TGA Q500). Next the sample is exposed to a temperature ramp that comprises from an initial temperature of 25° C., a heating ramp of 10° C. per minute, to a final temperature of 600° C. A graph of sample mass loss versus temperature is plotted to gain insights into transitions—water evaporation, volatile active evaporation, degradation of the microcapsule materials.

Differential Scanning calorimetry

Approximately 5 milligrams of sample is weighed onto a pan of a Differential Scanning calorimeter (Model DSC Q2000) and hermetically sealed. The sample pan is then exposed to a temperature ramp that comprises from an initial temperature of 25° C., a heating ramp of 10° C. per minute, to a final temperature of 250° C., and then a temperature decrease ramp of negative 10° C. per minute, to a final temperature of 25° C. A graph of heat flow versus temperature provides insights into thermal transitions that occur in the powder.

Scanning Electron Microscopy

A Phenom Pure (Nanoscience Instruments Model PW-100-019) Scanning Electron Microscope is used to understand the particle morphology, and nature of particle deposits on fabrics. PELCO tabs carbon tape (12 mm OD, Ted Pella product number 16084-1) is applied to an aluminum specimen mount (Ted Pella Product No 16111). Next, the powder sample is placed onto the carbon tape using a transfer spatula. Excess powder is removed by blowing Dust-Off compressed gas onto the sample. The stub is then left in a desiccator under vacuum for 16 hours to flash off any volatiles. The sample is then placed into the Phenom Pure, and imaged to visualize particle morphology.

High Pressure Liquid Chromatography

USP Monograph for Beta-Carotene, USP 39-NF 34

Biodegradability

Biodegradability testing is carried out according to protocol OECD 301D. 5 mg/L material is placed into BOD bottles in water collected from the Lehigh River (Bethlehem, Pa.). The bottles are checked for dissolved oxygen at 0, 7, 14, and 28 days. Intermittent points can also be taken since an asymptotic value may be reached much sooner than 28 days. The percent degradation is analyzed against the positive control starch. See Example 24 for a detailed description of the analysis and calculations of Biodegradability Index.

Example 1: Starch Encapsulated Vitamin—Control 84.4 g of HICAP 100 modified starch (Ingredion) is added to 253.3 g of water at 24° C. to make approximately a 25% wt. % solution.

The mixture is agitated at 600 RPM using a RW20 digital mixer with a turbine, 4-pitched blade impeller 2 inches in diameter, for 20 minutes and heated to 72° C.

3.12 g ascorbic acid is added to the starch and water solution.

11.7 g vitamin and 1.7 g alpha-tocopherol is added to a 21.11 g carrier oil heated to the vitamin melting temperature. The mixture is agitated until the vitamin is melted.

34.5 g vitamin-containing oil is added near the vortex of the starch solution.

The emulsion is homogenized at 20,000 RPM for 5 minutes using a Unidrive X1000 homogenizer with a rotor-stator shaft.

Upon achieving an oil phase with droplet median volume average diameter of less than 5 microns, the emulsion is pumped to a spray drying tower and atomized using a centrifugal atomizer with co-current airflow for drying. The inlet air temperature is set at 185-205° C., the exit air temperature is stabilized at 85-103° C.

Dried particles of the polysaccharide encapsulated vitamin oil are collected from the cyclone.

Example 2—Wax Incorporation in Core 84.4 g of HICAP 100 modified starch (Ingredion) is added to 253.3 g of water at 24° C. to make approximately a 25% wt. % solution.

The mixture is agitated at 600 RPM using a RW20 digital mixer with a turbine, 4-pitched blade impeller 2 inches in diameter, for 20 minutes and heated to 82° C.

3.12 g ascorbic acid is added to the starch and water solution.

11.7 g vitamin and 1.7 g alpha-tocopherol is added to a 16.0 g carrier oil heated to the vitamin melting temperature. The mixture is agitated until the vitamin is melted.

8.9 g rice bran wax is added to the oil phase and agitated until the wax is melted.

34.5 g vitamin-containing oil is added near the vortex of the starch solution.

The emulsion is homogenized at 20,000 RPM for 5 minutes using a Unidrive X1000 homogenizer with a rotor-stator shaft.

Upon achieving an oil phase with droplet median volume average diameter of less than 5 microns, the emulsion is pumped to a spray drying tower and atomized using a centrifugal atomizer with co-current airflow for drying. The inlet air temperature is set at 185-205° C., the exit air temperature is stabilized at 85-103° C.

Dried particles of the encapsulated vitamin oil are collected from the cyclone.

Example 3. Crosslinked Polysaccharide 51 g of HICAP 100 modified starch (Ingredion) is added to 182 g of water at 24° C. to make approximately a 25% wt. % solution.

8.62 g citric acid and 4.31 g sodium hypophosphite are added to the aqueous phase.

1.7 g ascorbic acid is added to the aqueous phase under mixing at 600 RPM.

The solution is agitated at 600 RPM using a RW20 digital mixer with a turbine, 4-pitched blade impeller 2 inches in diameter, for 20 minutes and heated to 82° C.

14.0 g beta-carotene, 2.1 g alpha-tocopherol, and 7.50 g rice bran wax are added to 25.5 g sunflower oil heated to the 155° C. The mixture is agitated until the vitamin is melted.

34.5 g vitamin-containing oil is added near the vortex of the starch solution.

The emulsion is homogenized at 20,000 RPM for 5 minutes using a Unidrive X1000 homogenizer with a rotor-stator shaft.

Upon achieving an oil phase with droplet median volume average diameter of less than 5 microns, the emulsion is pumped to a spray drying tower and atomized using a centrifugal atomizer with co-current airflow for drying. The inlet air temperature is set at 185-205° C., the exit air temperature is stabilized at 85-103° C.

Dried particles of the polysaccharide encapsulated vitamin oil are collected from the cyclone.

Silica flow aid is added at 1.5 wt. % level to the collected powder provide a modified powder.

The modified powder is heated to 150° C. for 30 minutes to form the controlled release particles.

Examples 4A-4G—Second Shell: Mannitol, Methocel, CMC, CMCS

In Example 4A, 150 g particles from Example 3 are resuspended in 400 g 15 wt. % Methocel E3 hydroxypropyl methylcellulose. The spray-ready suspension is spray-dried to provide a powder.

In Example 4B, the procedures of Example 4A are repeated with the Methocel E3 replaced by 350 g of 5 wt. % mannitol in water.

In Example 4C, the procedures of Example 4A are repeated with the Methocel E3 replaced by 350 g of 2 wt. % carboxymethyl cellulose.

In Example 4D, the procedures of Example 4A are repeated with the Methocel E3 replaced by 350 g of 2 wt. % carboxymethyl chitosan In Example 4E, the procedures of Example 4A are repeated with the Methocel E3 replaced by 350 g of 5 wt. % Methocel E15.

In Example 4F, the procedures of Example 4A are repeated with the Methocel E3 replaced by 350 g of 5 wt. % Methocel E50.

In Example 4G, the procedures of Example 4A are repeated with the Methocel E3 replaced by a solution containing 0.6 wt % xanthan gum and 0.9 wt. % konjac gum in water.

Example 5—Shell with Oxygen and Water Barrier Properties 105 g of zein is dissolved in 1350 g of 85% aqueous ethanol.

12.5 g beta-carotene and 1.9 g alpha-tocopherol is mixed into 25 g sunflower oil at 155° C. under a blanket of inert gas and stirred until the beta-carotene crystals are melted.

37.5 mL oil phase containing the vitamin is added into the heated zein solution held at 82° C. and stirred at 1000 rpm. 7.5 mL of 10% pea protein isolate is added.

The emulsion is held at 82° C. and homogenized at 20,000 RPM for 5 minutes using a Unidrive X1000 homogenizer with a rotor-stator shaft to provide a modified emulsion containing hydrophobic active ingredient droplets with a volume average diameter of less than 5 microns.

The suspension is removed from heat and water is added dropwise while agitating the mixture, at such a rate that the zein precipitates onto the oil phase forming a shell.

Water is added further such that the particles agglomerate into larger particles.

The solid particles are precipitated from the liquid.

The particles are resuspended in water to create a spray-ready suspension.

The spray-ready suspension is spray-dried to provide a powder.

Examples 6A-6G—Second Shell to Improve Barrier Properties

In Example 6A, 150 g particles from Example 5 are resuspended in 400 g 15 wt. % Methocel E3 hydroxypropyl methylcellulose. The spray-ready suspension is spray-dried to provide a powder.

In Example 6B, the procedures of Example 6A are repeated with the Methocel E3 replaced by 350 g of 5 wt. % mannitol in water.

In Example 6C, the procedures of Example 6A are repeated with the Methocel E3 replaced by 350 g of 2 wt. % carboxymethyl cellulose.

In Example 6D, the procedures of Example 6A are repeated with the Methocel E3 replaced by 350 g of 2 wt. % carboxymethyl chitosan.

In Example 6E, the procedures of Example 6A are repeated with the Methocel E3 replaced by 350 g of 5 wt. % Methocel E15.

In Example 6F, the procedures of Example 6A are repeated with the Methocel E3 replaced by 350 g of 5 wt. % Methocel E50.

In Example 6G, the procedures of Example 6A are repeated with the Methocel E3 replaced by a solution containing 0.6 wt. % xanthan gum and 0.9 wt. % konjac gum in water.

Example 7—Using Glycerol as a Solvent for Zein 2 g of zein is added to 50 g of glycerol heated to 150° C. with stirring.

The mixture is stirred for 10 minutes at 250 rpm to dissolve the zein.

0.6 g of beta carotene and 0.6 g of α-tocopherol are added to 1 g sunflower oil heated to 155° C. under a blanket of inert gas at 250 rpm.

0.3 g rice bran wax is added to the mixture of beta-carotene, alpha-tocopherol, and sunflower oil at 250 rpm.

The oil phase is mixed into the zein solution and agitated at 20,000 RPM for 4 minutes using a Unidrive X1000 rotor-stator mixer 150° C.-160° C. to provide an emulsion containing hydrophobic active ingredient droplets with a volume average diameter of less than 5 microns.

While stirring the mixture at 250 rpm, the temperature is decreased such that the zein precipitates onto the oil phase forming a shell and discrete particles.

Alternative to filtration of the particles, 26 wt. % silica flow aid is added to the suspension based on the weight of glycerol in the suspension and the mixture spray-dried.

Alternative to drying, the particles are precipitated and separated from the glycerol.

Alternatively, the particles are filtered and resuspended in an aqueous polymer solution to create a spray-ready suspension.

The suspension is pumped to a spray drying tower and atomized using a centrifugal atomizer with co-current air-flow for drying. The inlet air temperature is set at 185-205° C., the exit air temperature is stabilized at 85-103° C.

Dried particles of the vitamin in oil encapsulated in zein and a polymer shell are collected from the cyclone.

Examples 8A-8G: Zein Particles Using Glycerol as Solvent

In Example 8A, 150 g particles from Example 7 are resuspended in 400 g of 15 wt. % Methocel E3 hydroxypropyl methylcellulose. The spray-ready suspension is spray-dried to provide a powder.

In Example 8B, the procedures of Example 8A are repeated with the Methocel E3 replaced by 350 g of 5 wt. % mannitol in water.

In Example 8C, the procedures of Example 8A are repeated with the Methocel E3 replaced by 350 g of 2 wt. % carboxymethyl cellulose.

In Example 8D, the procedures of Example 8A are repeated with the Methocel E3 replaced by 350 g of 2 wt. % carboxymethyl chitosan.

In Example 8E, the procedures of Example 8A are repeated with the Methocel E3 replaced by 350 g of 5 wt. % Methocel E15.

In Example 8F, the procedures of Example 8A are repeated with the Methocel E3 replaced by 350 g of 5 wt. % Methocel E50.

In Example 8G, the procedures of Example 8A are repeated with the Methocel E3 replaced by a solution containing 0.6 wt % xanthan gum and 0.9 wt. % konjac gum in water.

Example 9: Aqua Zein 22.5 g soya wax is mixed with 1.4 g alpha-tocopherol and heated to 50° C. with agitation.

9.5 g retinyl palmitate is added to the wax and antioxidant mixture under a blanket of inert gas.

The solution of wax, vitamin, and antioxidant is mixed into 250 g AquaZein at 50° C. with agitation at 350 rpm to provide a pre-emulsion.

The pre-emulsion is agitated at 20,000 RPM for 4 minutes using a Unidrive X1000 rotor-stator mixer 50° C. to provide an emulsion containing hydrophobic active ingredient droplets with a volume average diameter of less than 5 microns.

Remove from heat and stir at 1000 RPM.

250 mL total 7.5% Methocel E50 is added dropwise to the emulsion under stirring, alternated with 800 mL total water, to precipitate AquaZein onto hydrophobic droplets. 0.5 g nanosilica is added periodically during addition of water to prevent clumping during addition of water.

Stirring is continued until suspension is cooled to below 28 C.

The emulsion is spray dried to provide a powder.

Examples 10A-10G—Aqua Zein Particles with Second Shell

In Example 10A, 150 g particles from Example 9 are resuspended in 400 g 15 wt. % Methocel E3 hydroxypropyl methylcellulose. The spray-ready suspension is spray-dried to provide a powder.

In Example 10B, the procedures of Example 10A are repeated with the Methocel E3 replaced by 350 g of 5 wt. % mannitol in water.

In Example 10C, the procedures of Example 10A are repeated with the Methocel E3 replaced by 350 g of 2 wt. % carboxymethyl cellulose.

In Example 10D, the procedures of Example 10A are repeated with the Methocel E3 replaced by 350 g of 2 wt. % carboxymethyl chitosan.

In Example 10E, the procedures of Example 10A are repeated with the Methocel E3 replaced by 350 g of 5 wt. % Methocel E15.

In Example 10F, the procedures of Example 10A are repeated with the Methocel E3 replaced by 350 g of 5 wt. % Methocel E50.

In Example 10G, the procedures of Example 10A are repeated with the Methocel E3 replaced by a solution containing 0.6 wt % xanthan gum and 0.9 wt. % konjac gum in water.

Example 11. Stability Testing of Various Powders

High Performance Liquid Chromatography (HPLC) is used to quantify the stability of the particles. Powders are stressed following ICH guidelines. Particles mixed with vitamin premix are exposed to different humidity levels (28% RH, 62% RH, 80% RH) in the dark at room temperature, and compared to a no treatment condition in a closed vial. As temperature and light were not found to cause significant degradation, these conditions were held constant.

While the invention has been described in detail and with reference to specific examples thereof, it will be apparent to one skilled in the art that various changes and modifications can be made therein without departing from the spirit and scope thereof.

What is claimed is:

1. Controlled release particles comprising:

(a) a core comprising at least one vitamin which is oil-soluble or oil-dispersible; and (b) a wall at least partially surrounding the core and comprising a corn protein and a cellulosic polymer, wherein the controlled release particles are produced by reacting (i) a core-forming composition comprising a hydrophobic oil, the at least one vitamin, an anti-oxidant, an oil soluble emulsifier, and a wax, with (ii) a corn protein composition comprising the corn protein to form an intermediate product, which is then mixed with (iii) a cellulosic polymer composition comprising the cellulosic polymer in water, and dehydrated to provide the controlled release particles, wherein the controlled release particles have a median particle diameter from 0.1 micrometers to 100 micrometers.

2. The controlled release particles of claim 1 comprising 1.9-22 wt. % of the at least one vitamin in the core, 3-37% wt. % of the hydrophobic oil in the core, 1.8-22% wt. % of the anti-oxidant in the core, 4.6-55.4 wt. % of the corn protein in the wall, 1-3.15 wt. % of the cellulosic polymer in the wall, up to 11 wt. % of the wax in the core, and further comprising up to 4 wt. % of a silica flow aid in the wall, optionally 1-11.5 wt. % of a polysaccharide in the wall and optionally up to 0.4% pea protein in the wall, wherein the controlled release particles are anhydrous and the at least one vitamin is encapsulated in a polymer matrix effective to retain an activity of the at least one vitamin upon exposure to water, oxygen, light and heat.

3. The controlled release particles of claim 1 comprising 4-30 wt. % of the at least one vitamin in the core, 7-60% wt. % of the hydrophobic oil in the core, 0.6-4.4 wt. % of the anti-oxidant in the core, 3-21.7 wt. % of the corn protein in wall, up to 1-9.4 wt % of the wax in the core, 1.7-4 wt. % of an oil soluble emulsifier in the core, 14-40 wt. % of a polysaccharide in the wall, up to 3 wt % of the cellulosic polymer in the wall, and further comprising 1-9.4 wt. % of a silica flow aid in the wall, and optionally 0.6-3 wt. % of a water soluble antioxidant in the wall, wherein the controlled release particles are anhydrous and the oil soluble vitamin is encapsulated in a polymer matrix effective to retain the oil soluble vitamin activity upon exposure to water, oxygen, light and heat.

4. The controlled release particles of claim 1, wherein the at least one vitamin is at least one member selected from the group consisting of Vitamin A, Vitamin D, Vitamin E and Vitamin K.

5. The controlled release particles of claim 1, wherein the at least one vitamin is provided in a form of a fish liver oil containing Vitamin A and/or D, a synthetic Vitamin A palmitate and/or acetate concentrated in an oil solution, a Vitamin D oil solution, a Vitamin D oleaginous resin, a Vitamin E oil solution, a Vitamin K oil solution, or a crystalline suspension of beta-carotene in oil.

6. The controlled release particles of claim 1, wherein the hydrophobic oil is a member selected from the group consisting of a flavorant, an essential oil, a sweetener, an active pharmaceutical ingredient, a vitamin oil, a vegetable oil, and a triglyceride.

7. The controlled release particles of claim 1, wherein the anti-oxidant is a member selected from the group consisting of Vitamin A, Vitamin C, Vitamin E, folic acid, (Beta-carotene), Coenzyme Q10, alpha-tocopherol and polyphenols.

8. The controlled release particles of claim 1, wherein the cellulosic polymer is a member selected from the group consisting of naturally derived polymers with a cellulose backbone that have a solubility in water greater than 1 wt. %.

9. The controlled release particles of claim 2, wherein the polysaccharide is a member selected from the group consisting of octenyl succinic acid anhydride modified starch, gum arabic, xanthan gum, gellan gum, pectin gum, konjac gum and carboxyalkyl cellulose.

10. The controlled release particles of claim 2, wherein the silica flow aid is a member selected from the group consisting of fumed silica, precipitated silica, calcium silicate, aluminosilicate, and combinations thereof.

11. The controlled release particles of claim 1, having an Environmental Degradability index greater than 80.

12. The controlled release particles of claim 1, wherein the hydrophobic oil ingredient comprises a mixture of a hydrophobic active and a material selected from the group consisting of plant waxes, animal waxes, petroleum based waxes, synthetic waxes, mineral waxes, brominated oils, hydrophobically modified inorganic particles, nonionic emulsifiers and oil thickening agents.

13. A composition comprising the controlled release particles of claim 1, wherein the composition is a powdered food product, a fluid food product, a powdered nutritional supplement, a fluid nutritional supplement, a fluid fabric enhancer, a solid fabric enhancer, a fluid shampoo, a solid shampoo, hair conditioner, body wash, solid antiperspirant, fluid antiperspirant, solid deodorant, fluid deodorant, fluid detergent, solid detergent, a diaper, a nutraceutical supplement, a skin care product, a baby care product, a family care product, a feminine care product or a household care product.

14. The composition of claim 13, further comprising at least one suspension agent to suspend the controlled release particles, wherein the at least one suspension agent is at least one member selected from the group consisting of a rheology modifier, a structurant and a thickener.

15. The composition of claim 14, wherein the at least one suspension agent has a high shear viscosity, at 20 $sec^{-1}$ shear rate and at 21° C., of from 1 to 7000 cps and a low shear viscosity, at 0.5 $sec^{-1}$ shear rate at 21° C., of greater than 1000 cps.

16. The composition of claim 14, which has a high shear viscosity, at 20 $sec^{-1}$ and at 21° C., of from 50 to 3000 cps and a low shear viscosity, at 0.5 $sec^{-1}$ shear rate at 21° C., of greater than 1000 cps.

17. The composition of claim 14, wherein the at least one suspension agent is selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

18. The composition of claim 13, having at least two controlled release technologies, which release different hydrophobic oil compositions and are selected from the group consisting of neat oils, friction-triggered release microcapsules and water-triggered release microcapsules.

* * * * *